(12) United States Patent
Tsai et al.

(10) Patent No.: US 7,101,710 B2
(45) Date of Patent: Sep. 5, 2006

(54) TWO-STAGE CULTURE PROTOCOL FOR ISOLATING MESENCHYMAL STEM CELLS FROM AMNIOTIC FLUID

(76) Inventors: Ming-Song Tsai, 5F, No.5, Alley 25, Lane 300, Section 4, Jeu-Ai Road, Taipei (TW); Shiaw-min Hwang, No.25, Alley 1, Lane 30, Fu-Chin Street, Hsinchu 300 (TW)

( * ) Notice: Subject to any disclaimer, the term of this patent is extended or adjusted under 35 U.S.C. 154(b) by 94 days.

(21) Appl. No.: 10/847,582

(22) Filed: May 18, 2004

(65) Prior Publication Data

US 2005/0118712 A1    Jun. 2, 2005

(30) Foreign Application Priority Data

Dec. 2, 2003    (TW) .............................. 92133931 A (51) Int. Cl.
*C12N 5/08*    (2006.01)
*C12P 19/34*    (2006.01)
*G01N 33/53*    (2006.01)

(52) U.S. Cl. .................. 435/378; 435/366; 435/383; 435/384; 435/395; 435/91.2; 435/7.1

(58) Field of Classification Search .............. 435/378, 435/383, 325, 366
See application file for complete search history.

(56) References Cited

U.S. PATENT DOCUMENTS

2005/0042595 A1 * 2/2005 Haas .............................. 435/2

2005/0124003 A1 * 6/2005 Atala et al. ................... 435/7.2

OTHER PUBLICATIONS

Kaviani et al. The amniotic fluid as a source of cells for fetal tissue engineering. Journal of Pediatric Surgery. 36(11):1662-1665, Nov. 2001.*

Prusa et al. Amniotic fluid cells and human stem cell research—a new connection. Medical Science Monitor. 8(11):RA253-RA257, 2002.*

* cited by examiner

*Primary Examiner*—Terry McKelvey
*Assistant Examiner*—Jennifer Dunston
(74) *Attorney, Agent, or Firm*—Rosenberg, Klein & Lee

(57) ABSTRACT

A method of harvesting mesenchymal stem cells from human amniotic fluid uses a two-stage culture protocol comprising culturing human amniocytes and then culturing mesenchymal stem cells. For culturing human amniocytes, primary amniocyte cultures are set up using routine or standard culture protocol in a cytogenetic laboratory. Non-adherent human amniotic fluids cells in the supernatant medium are collected. For culturing mesenchymal stem cells ("MSC"), the non-adherent cells are centrifuged and then plated with an alpha-modified Minimum Essential Medium supplemented with fetal bovine serum. Incubate with humidified $CO_2$ for MSC growth. Reverse transcription polymerase chain reaction ("RT-PCR") and immunocytochemical analyses reveal that Oct-4 mRNA and OCT-4 protein expression is detectable in the cultured amniotic fluid mesenchymal stem cells ("AFMSCs"). Under differentiation culture conditions, the AFMSCs can be induced to develop into multi-lineage cells, such as adipocytes, osteocytes, neuronal cells, etc.

21 Claims, 6 Drawing Sheets
(4 of 6 Drawing Sheet(s) Filed in Color)

TWO-STAGE CULTURE PROTOCOL FOR ISOLATING MESENCHYMAL STEM CELLS FROM AMNIOTIC FLUID

BACKGROUND OF THE INVENTION

1. Field of the Invention

The present invention relates to human stem cells. More specifically, the present invention discloses a method of isolating mesenchymal stem cells from amniotic fluid using a two-stage culture protocol.

2. Description of the Prior Art

Stem cells are cells that have the capability of renewing themselves through cell division. They can also be induced to become cells with special functions. Two kinds of stem cells are embryonic stem cells and adult stem cells.

The importance of stem cells to humans is immense. For example, in a developing fetus, stem cells result in specialized cell types that make up vital organs such as skin, the heart, and lungs. Furthermore, research is being conducted that may result in stem cells being used to treat fatal diseases such as heart disease, Parkinson's disease, and diabetes.

However, some people have reservations about ethically using stem cells from human embryos or human fetal tissue.

Since there are many ethical concerns with human embryonic stem cells, looking for a feasible way to obtain fetal pluripotent stem cells has generated a great deal of interest from researchers. Although mesenchymal stem cells ("MSCs") have been isolated successfully from first-trimester fetal blood, liver, spleen and bone marrow, their use in research and therapeutics is also encumbered with ethical considerations and difficult access with minute quantities.

Therefore, there is need for a method of obtaining amniotic fluid-derived MSCs ("AFMSCs") which provide a superior alternative source for MSC research without the limitations mentioned above.

SUMMARY OF THE INVENTION

To achieve these and other advantages and in order to overcome the disadvantages of the conventional method in accordance with the purpose of the invention as embodied and broadly described herein, the present invention provides a method of isolating human multipotent mesenchymal stem cells from amniotic fluid using a two-stage culture protocol.

The present invention demonstrates that MSCs are present in human amniotic fluid and a novel two-stage culture method was developed to successfully isolate, culture, and enrich MSCs from amniotic fluid for example second trimester amniotic fluid obtained by routine amniocentesis for prenatal diagnosis. There are at least four major advantages of this culture protocol for fetal MSCs. First, it does not interfere with the normal culture process for fetal karyotyping. Secondly, it does not raise any ethical issues that are associated with human embryonic stem cell research. Thirdly, it provides an unprecedented and abundant source for research on human MSCs. Fourthly, it opens a new avenue for autologous intrauterine fetal gene and cellular therapies without inducing tissue rejection.

MSCs can be isolated and expanded from 2 ml second-trimester amniotic fluid, which was collected transcervically from terminations of pregnancy and shows multilineage potential for differentiation into adipocytes and osteocytes. However, there are several disadvantages in collecting amniotic fluid through the cervix compared with through the abdomen by routine second-trimester amniocentesis: first, it might possibly encourage illegal termination of pregnancy. Secondly, the transcervical approach could increase possibility of contamination. Thirdly, the amount of MSCs isolated from 2 ml amniotic fluid culture is far less than that from the two-stage culture protocol of the present invention. Therefore, utilization of the present invention avoids these disadvantages.

It has been proposed that stem cells of all three germ layers (ectoderm, mesoderm and endoderm) can be detected in human amniotic fluid, while very little is known about their lifespan throughout pregnancy. Under routine conditions for fetal karyotyping, amniotic fluid cells ("AFCs") can be divided into two major categories: adhering and non-adhering cells. Furthermore, AFCs can also be classified according to their morphological aspects and growth characteristics into three groups: epitheloid E-type cells; amniotic fluid specific AF-type cells; and fibroblastic F-type cells. The fibroblastic F-type cells have been considered to originate from mesenchymal tissue and usually appear late during routine AFC cultivation.

As a result of research and analysis, the inventors have determined that the AFMSCs isolated by the two-stage culture protocol of the present invention are most likely to be the fibroblastic F-type cells in the amniotic fluid and have confirmed that they are mesenchymal in origin.

AFMSCs have phenotypic characteristics similar to those of MSCs derived from other sources, such as term umbilical cord blood and first-trimester fetal tissues (blood, liver and bone marrow), which are positive for SH2, SH3, SH4, CD29, CD44 and HLA-A,B,C, and negative for CD10, CD11b, CD14, CD34, CD117, EMA and HLA-DR,DP,DQ. Most importantly, AFMSCs express Oct-4 mRNA and Oct-4 protein, a transcription factor expressed in embryonic carcinoma cells, embryonic stem cells and embryonic germ cells, reflecting a key role in the maintenance of pluripotency of mammalian stem cells both in vivo and in vitro. Findings confirm that there were Oct-4 expressing cells in human amniotic fluid and suggest that human amniotic fluid might contain stem cells of high potency.

The AFMSCs described here can be expanded rapidly and they maintain the capacity to differentiate into multiple cell types in vitro. Aside from the common mesenchymal lineages (adipocytes and osteocytes), they also have been differentiated successfully into neuronal cells. These findings are encouraging and describe that marrow stromal cells could be differentiated into multiple mesodermal cell types and neuron-like cells that expressed neuronal markers, suggesting that MSCs may be capable of overcoming germ layer commitment. Whether AFMSCs have the ability to differentiate into lineages of endoderm in vitro is an issue that is worth investigating.

It has been shown that MSCs represented an attractive population for cellular therapy protocols, such as repairing infracted myocardium, improving angiogenesis of stroke and repairing bone damage. Traditionally, the main sources of MSCs are isolated from postnatal origins, including adult bone marrow, umbilical cord blood, peripheral blood and various mesenchymal tissues (muscle, bone, cartilage, tendon, vessels and adipose). Current evidence suggests that aside from being difficult to obtain, adult stem cells have disadvantages of markedly restricted differentiation potential, decreasing number with age, more DNA damage and shorter life span compared with pluripotent stem cells derived from embryos or fetal tissue. Since there are many ethical concerns with human embryonic stem cells, looking for a feasible way to obtain fetal pluripotent stem cells has generated a great deal of interest from researchers. Although MSCs have been isolated successfully from first-trimester fetal blood, liver, spleen and bone marrow, their use in research and therapeutics is also encumbered with ethical considerations and difficult access with minute quantities.

In contrast, the AFMSCs obtained by the two-stage culture protocol of the present invention may be a superior alternative source for MSC research without the limitations mentioned above. However, it remains a very interesting issue to be elucidated in the near future whether AFMSCs have greater therapeutic potential than that of the current adult MSCs.

The present invention provides a method for isolating mesenchymal stem cells from amniotic fluid using a two-stage culture protocol. The two-stage culture protocol comprises a first stage of culturing amniocytes, and a second stage of culturing mesenchymal stem cells.

The method for culturing amniocytes begins by setting up primary cultures using cytogenetic laboratory routine or standard amniocytes culture protocol, for example, setting up cultures in culture-grade dishes using Chang medium. Non-adhering amniotic fluid cells in the supernatant are collected. For culturing mesenchymal stem cells, the non-adhering cells are centrifuged and plated with an alpha-modified Minimum Essential Medium supplemented with fetal bovine serum in a culture flask and incubated with humidified $CO_2$ for MSC growth. Flow cytometry, reverse transcription polymerase chain reaction ("RT-PCR"), and immunocytochemcial analyses are performed for phenotypic characteristic analyses of the AFMSCs.

The present invention demonstrates that MSCs can be successfully isolated and expanded from second-trimester amniotic fluid obtained by routine amniocentesis, and they maintain the capacity to differentiate not only into mesodermal cell types but also into ectodermal neuron cells in vitro. Considering the easy access to samples for stem cells culture, the greater potential of cellular therapy using fetal stem cells and the feasibility of intrauterine fetal tissue engineering, amniotic fluid may provide an excellent alternative source for investigation of human MSCs and their potential therapeutic applications.

These and other objectives of the present invention will become obvious to those of ordinary skill in the art after reading the following detailed description of preferred embodiments.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

FIG. 1B is an image showing the fibroblastic-like AFMSC colonies which grew to confluence in the first-passage culture;

FIG. 1C is an image showing Adipogenic differentiation demonstrated by Oil Red O staining;

FIG. 1D is an image showing Osteogenic differentiation demonstrated by von Kossa staining;

FIG. 2B is an image showing the cytoplasm of the cells retract toward the nucleus and forms a rounded cell body after 6 hours of pre-treatment;

FIG. 2C is an image showing an apparent neuron-like cell with a long axon-like process observed after 4 hours of serum-free induction;

FIG. 2D is a diagram showing a typical neuron-like cell with multiple neuritis after 4.5 hours of serum-free induction;

FIG. 2E is an image showing a neuron-like cell before staining;

FIG. 2F is an image showing positive immunofluorescence stain of TuJ1, a marker for neuronal differentiation;

FIG. 5B is an image showing Oct-4 immunocytochemical staining of NTERA-2 c1.D1 cells;

FIG. 5C is an image showing the light phase of AFMSCs;

FIG. 5D is an image showing immunocytochemical staining of Oct-4 positive cells in cultured AFMSCs.

The file of this Patent contains at least one drawing executed in color. Copies of this Patent with color drawings will be provided by the Patent and Trademark Office upon request and payment of the necessary fee.

DESCRIPTION OF THE PREFERRED EMBODIMENTS

Reference will now be made in detail to the preferred embodiments of the present invention, examples of which are illustrated in the accompanying drawings. Wherever possible, the same reference numbers are used in the drawings and the description to refer to the same or like parts.

Human mesenchymal stem cells (MSCs) are thought to be multipotent cells that have the potential to differentiate into multiple lineages including bone, cartilage, muscle, tendon, ligament fat and a variety of other connective tissues. Morphologically, MSCs in their undifferentiated state are spindle shaped and resemble fibroblasts. MSCs have been identified mostly in adult bone marrow, while MSCs are also present in both adult and fetal peripheral blood, fetal liver, fetal spleen, placenta and in term umbilical cord blood.

To date, little is known about whether MSCs are present in human amniotic fluid or not, despite culturing of amniotic fluid cells being a well-established routine procedure in cytogenetic laboratories. Multiple approaches have been used to characterize and classify the cell types of amniotic fluid, yet many questions concerning the nature and in vivo origin of these cells have not been entirely resolved.

Recently, some reports have mentioned that amniotic fluid contains a variety of human stem cells, which were shed from embryonic and extra-embryonic tissues during the process of fetal development and growth. Human amniotic fluid epithelial cells could transform into neurons, astrocytes and oligodenrocytes, and the cell might be a possible candidate for transplantation therapy of neurodegenerative diseases. Amniotic fluid is an attractive source of MSCs for therapeutic transplantation. Furthermore, Oct-4-expressing cells were present in human amniotic fluid, and it was proposed that human amniotic fluid might be a new source for pluripotent stem cells without raising any ethical concerns associated with human embryonic stem cells research.

Figure 6:
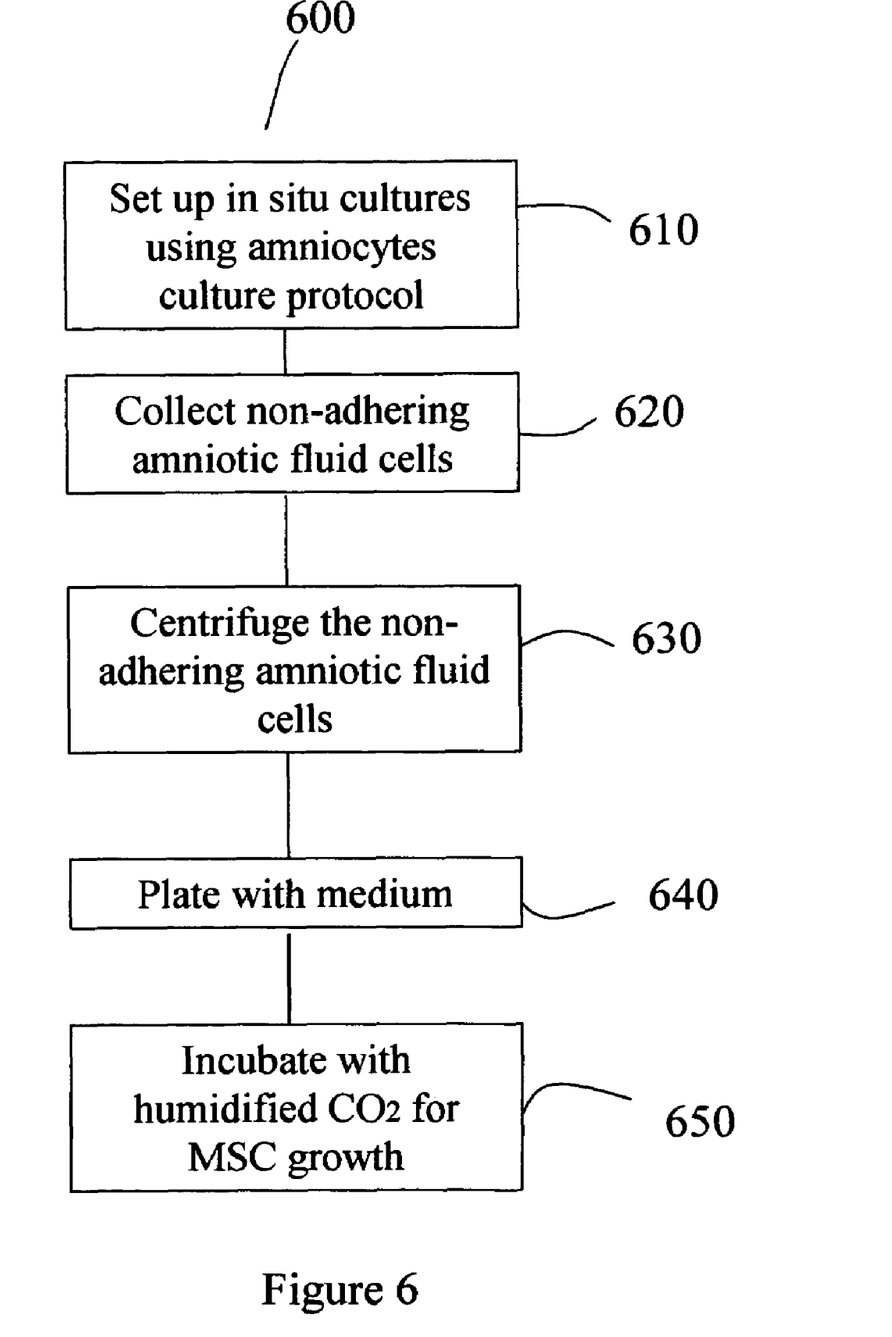
FIG. 6 is a flowchart illustrating a method for isolating mesenchymal stem cells from amniotic fluid using a two-stage culture protocol according to an embodiment of the present invention.

Refer to FIG. 6, which is a flowchart illustrating a method for isolating mesenchymal stem cells from amniotic fluid using a two-stage culture protocol according to an embodiment of the present invention.

The two-stage culture protocol comprises a first stage of culturing amniocytes, and a second stage of culturing mesenchymal stem cells.

As shown in FIG. 6, the method 600 begins in Step 610 for culturing amniocytes by setting up primary cultures using cytogenetic laboratory amniocytes culture protocol. In Step 620, non-adhering amniotic fluid cells in the supernatant medium are collected. In Step 630, for culturing mesenchymal stem cells, centrifuge the non-adhering cells and in Step 640, plate them with an alpha-modified Minimum Essential Medium supplemented with fetal bovine serum in a culture flask. In Step 650, incubate with humidified $CO_2$ for MSC growth.

As an example of applying the method of the present invention the following is given. However, it should be noted that various modifications such as substitute materials, medium, quantities, temperature, etc. are also included without varying from the scope of the present invention.

For culturing amniocytes, set up four primary cultures in 35 mm tissue culture grade dishes using Chang medium (Irvine Scientific, Santa Ana, Calif.). Collect non-adhering amniotic fluid cells in the supernatant medium on the $5^{th}$ day alter the primary amniocytes culture and keep them until completion of fetal chromosome analysis.

For culturing mesenchymal stem cells, centrifuge the tube containing the non-adhering cells, then plate them in 5–15 ml of alpha-modified Minimum Essential Medium ("α-MEM") supplemented with 10–20% fetal bovine serum ("FBS") and 1–20 ng/ml b-FGF in a 25 $cm^2$ culture flask and incubate at 37° C. with 5% humidified $CO_2$ for MSC growth.

For characteristic analyses of the AFMSCs, flow cytometry analyses show that the AFMSCs from the protocol are positive for SH2, SH3, SH4, CD29, CD44 and HLA-ABC (MHC class I), low positive for CD90 and CD105, but negative for CD10, CD11b, CD14, CD34, CD117, HLA-DR, DP, DQ (MHC class II) and EMA. Importantly, RT-PCR and immunocytochemical analyses reveal that Oct-4 mRNA and Oct-4 protein expressions are detectable in the cultured AFMSCs. Under specific culture conditions, AFMSCs could be induced to differentiate into adipocytes, osteocytes and neuronal cells.

To verify the method of the present invention, a study was undertaken to isolate mesenchymal stem cells (MSCs) from amniotic fluid obtained by second-trimester amniocentesis.

In the study, it is shown that human MSCs can be isolated from amniotic fluid without interfering with the process of fetal karyotyping using a novel two-stage culture protocol. The cells isolated by this culture method have the capacity to differentiate into multiple cell types in vitro.

A novel two-stage culture protocol for culturing MSCs was developed. Flow cytometry, RT-PCR, and immunocytochemistry were used to analyse the phenotypic characteristics of the cultured MSCs. Von Kossa, Oil Red O and TuJ-1 stainings were used to assess the differentiation potentials of MSCs.

As a result of the study it was determined that Amniotic fluid-derived MSCs (AFMSCs) were successfully isolated, cultured, and enriched without interfering with the routine process of fetal karyotyping. Flow cytometry analyses showed that they were positive for SH2, SH3, SH4, CD29, CD44 and HLA-ABC (MHC class I), low positive for CD90 and CD105, but negative for CD10, CD11b, CD14, CD34, CD117, HLA-DR, DP, DQ (MHC class II) and EMA. Importantly, a subpopulation of Oct-4 positive cells was detectable in the cultured AFMSCs. Under specific culture conditions, AFMSCs could be induced to differentiate into adipocytes, osteocytes and neuronal cells.

It was demonstrated that human multipotent MSCs are present in amniotic fluid. Considering the greater potential of cellular therapy using fetal stem cells and the feasibility of intrauterine fetal tissue engineering, amniotic fluid may provide an excellent alternative source for investigation of human MSCs.

Following in a description of the materials and methods utilized in the study starting with the culture of MSC from amniotic fluid.

Twenty amniotic fluid samples (20 ml) were obtained by amniocentesis performed between 16 and 20 weeks of gestation for fetal karyotyping. A novel two-stage culture protocol was developed for harvesting MSCs from amniotic fluid. For culturing amniocytes (first stage), four primary cultures were set up in 35 mm tissue culture-grade dishes using Chang medium (Irvine Scientific, Santa Aria, Calif.). Microscopic analysis of Giemsa-stained chromosome banding was performed, and the rules for metaphase selection and colony definition were based on the basic requirements for prenatal cytogenetic diagnosis in amniocytes. For culturing MSCs (second stage), non-adhering amniotic fluid cells in the supernatant medium were collected on the fifth day after the primary amniocytes culture and kept until completion of the fetal chromosome analysis. The cells then were centrifuged and plated in 5 ml of alpha-modified Minimum Essential Medium (α-MEM, Gibco, BRL) supplemented with 20% fetal bovine serum (FBS, Hyclone, Logan, Utah) and 4 ng/ml basic fibroblast growth factor (b-FGF; R&D systems, Minneapolis, Minn.) in a 25-$cm^2$ flask and incubated at 37° C. with 5% humidified $CO_2$ for MSC culture. This protocol has been approved by the Institutional Review Board (IRB) of Cathay General Hospital and each patient signed a written informed consent.

For differentiation assay for MSCs, Amniotic fluid-derived mesenchymal stem cells (AFMSCs) were cultured to confluence and shifted to osteogenic medium (α-MEM supplemented with 10% FBS, 0.1 μmol/l dexamethason, 10 mmol/l β-glycerol phosphate, 50 μmol/l ascorbate) and adipogenic medium (α-MEM supplemented with 10% FBS, 1 μmol/l dexamethasone, 5 μg/ml insuline, 0.5 mmol/l isobutylmethylxanthine and 60 μmol/l indomethacin) for 3 weeks.

The differentiation potential for osteogenesis was assessed by the mineralization of calcium accumulation by von Kossa staining. For adipogenic differentiation, intracellular lipid droplets could be observed under microscope and confirmed by Oil Red O staining. For differentiation of neural cells, AFMSCs were incubated with—MEM supplemented with 20% FBS, 1 mmol/l β-mercaptoethanol, 5 ng/ml b-FGF (Sigma; St. Louis) for 24 h, and then treated with serum depletion for 5 h. Immunocytochemical stain with neuron-specific class III β-tubulin (TuJ-1) was used to assess the capacity of neuronal differentiation.

The specific surface antigens of AFMSCs in the cultures were characterized by flow cytometry analyses. The cells in culture were trypsinzed and stained with fluorescein-isothiocyanate (FITC)- or phycoerythrin (PE)-conjugated antibodies against CD10, CD11b, CD34, CD90, HLA-A,B,C, HLA-DR,DP,DQ (BD PharMingen); CD14, CD29, CD44, CD105, CD117 (Eurolone); and SH2, SH3, SH4 (American Type Culture Collection, Manassas, Va.). Thereafter, the cells were analysed using a Becton Dickinson flow cytometry (Becton Dickinson, San Jose, Calif.).

The following sequence description and listing, attached hereto as an Appendix to this Application as both a paper copy and a copy in computer readable form (CRF), are in accordance with U.S. Patent and Trademark Office Rules and Regulations as set forth in 37 CFR § 1.821–1.825.

For the RT-PCR procedure, the total RNA was extracted from cultured cells by using Tri Reagent (MRC Inc., Cincinnati, Ohio) according to the manufacturer's instructions. RT-PCR was performed using OneStep RT-PCR kit (QIAGEN Inc., Valencia, Calif.) using specific DNA primers as follows:

Oct-4 (247 bp) sense,

5'-CGTGAAGCTGGAGAAGGAGAAGCTG-3'    SEQ ID NO: 1;

anti-sense,

5'-CAAGGGCCGCAGCTTACACATGTTC-3'    SEQ ID NO: 2; and

β-actin (396 bp) sense,

5'-TGGCACCACACCTTCTACAATGAGC-3'    SEQ ID NO: 3;

anti-sense,

5'-GCACAGCTTCTCCTTAATGTCACGC-3'    SEQ ID NO: 4.

RT-PCR was performed initially at 50° C. for 30 min and 95° C. for 15 min for reverse transcription, then followed by 35 cycles, with each cycle consisting of denaturing at 94° C. for 1 min, annealing at 57° C. for 1 min, elongation at 72° C. for 1 min, and the final extension at 72° C. for 10 min.

The amplified DNA fragments were visualized through 2% agarose gel electrophoreses, stained and photographed under UV light. NTERA-2 c1.D1 cells (ATCC CRL-1973, a pluripotent human testicular embryonic carcinoma cell line) and MRC-5 cells (human diploid lung fibroblast, ATCC CCL-171) were used as positive and negative control for Oct-4 RT-PCR expression analysis, respectively.

For immunofluorescence analyses of cellular Oct-4 expression, the cultured AFMSCs, MRC-5 cells (negative control) and NTERA-2 c1.D1 cells (positive control) were washed, fixed, and incubated with 1:100 mouse anti-human Oct-4 monoclonal antibody (Santa Cruz Biotechnology, Santa Cruz, Calif.) overnight at 4° C. Thereafter, the cells were washed and incubated with a secondary antibody of fluoresceine isothiocyanate (FITC)-conjugated horse anti-mouse IgG (Vector Laboratories, Burlingame, Calif.) at room temperature for 1 h. Cell nuclei were counterstained with 1 µg/ml 4,6-diamino-2-phenylindole (DAPI, Molecular Probes, Eugene, Oreg.) in phosphate-buffered saline (PBS) for 5 min and mounted in VECTASHIELD mounting medium (Vector Laboratories).

For cellular neuron-specific class III β-tubulin analyses, the induced AFMSCs were washed, fixed, and incubated with 1:400 mouse anti-human β-tubulin III monoclonal antibody (Sigma; St. Louis, Mo.) overnight at 4° C. Thereafter, the cells were washed, incubated with a secondary antibody of FITC-conjugated horse anti-mouse IgG (Vector Laboratories, Burlingame, Calif.) at room temperature for 1 h and mounted in VECTASHIELD mounting medium (Vector Laboratories).

Figure 1A:
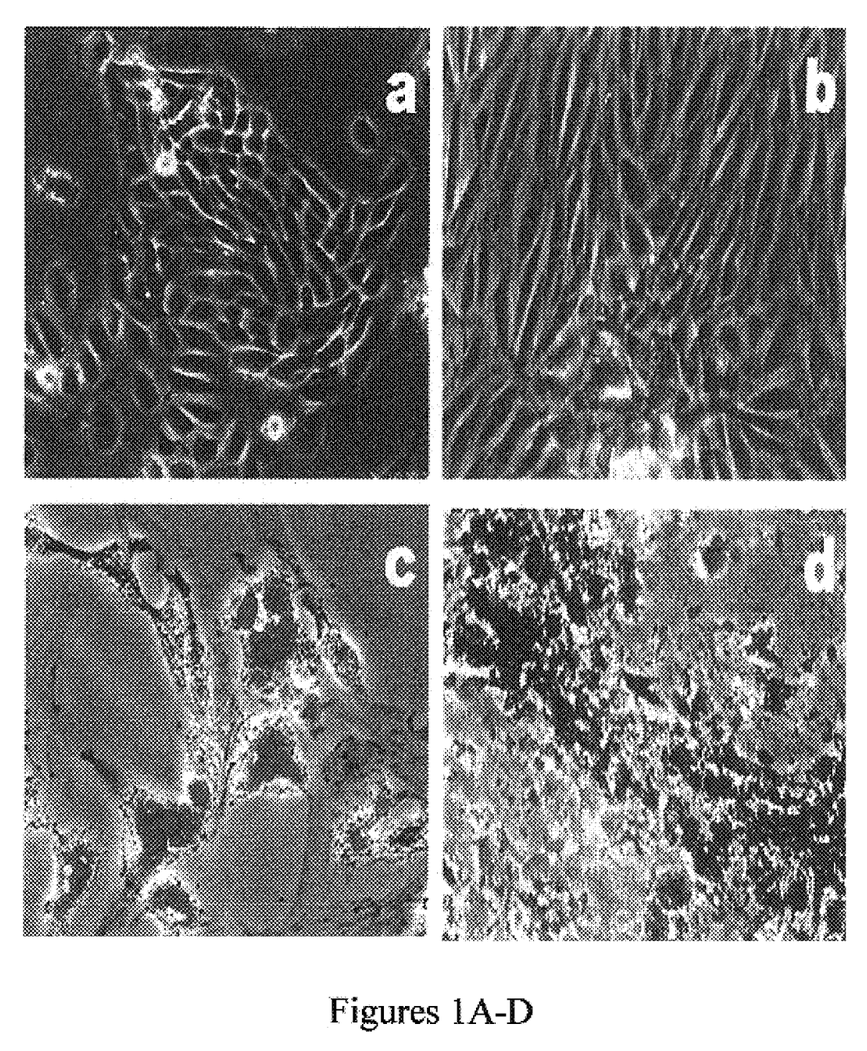
FIG. 1A is an image showing the appearance and growth of MSC-like cell colonies.

Refer to FIG. 1A, which is an image showing the appearance and growth of MSC-like cell colonies.

As shown in FIG. 1A, the colonies of MSC-like cells began to appear in the culture flask 5 days after plating the non-adhering amniotic fluid cells from primary amniocyte culture.

After 2 weeks culture, the cells were washed with PBS, treated with 0.05% trypsin-EDTA, and passed into a new 25 $cm^2$ flask for the first-passage culture.

Refer to FIG. 1B, which is an image showing the fibroblastic-like AFMSSC colonies which grew to confluence in the first-passage culture. As illustrated in FIG. 1B, these cells grew to 90% confluence of the culture (3–7 days). Then they were reseeded into a 75 $cm^2$ flask for the second-passage culture. The third and subsequent passages were carried on in 75 $cm^2$ flasks under the same condition at a split ratio 1:4. The twelfth-passage culture has been completed in the laboratory and their chromosome analyses remain as a normal karyotype of either 46,XX or 46,XY. Utilizing the present invention, MSC-like cells from every tested amniotic fluid samples (n=20) have been successfully cultured. To evaluate the differentiation potential of AFMSCs, cells at the third to fifth passage were induced to form adipocytes, osteocytes and neuronal cells. Adipogenic differentiation was apparent after 1 week of incubation with adipogenic induction medium.

Refer to FIG. 1C, which is an image showing Adipogenic differentiation demonstrated by Oil Red O staining.

As illustrated in FIG. 1C, between the culture periods of 2–3 weeks, almost all cells contained numerous Oil Red O positive lipid droplets.

Refer to FIG. 1D, which is an image showing Osteogenic differentiation demonstrated by von Kossa staining.

As illustrated in FIG. 1D, after culturing AFMSCs with osteogenic induction medium for 14 days, most of the cells became alkaline phosphatase positive and showed the aggregates or nodules of calcium mineralization in the culture by von Kossa staining.

To induce neural differentiation, AFMSCs were incubated in a serum-containing medium for 24 hours, and then treated with serum depletion for 5 hours.

Figure 2A:
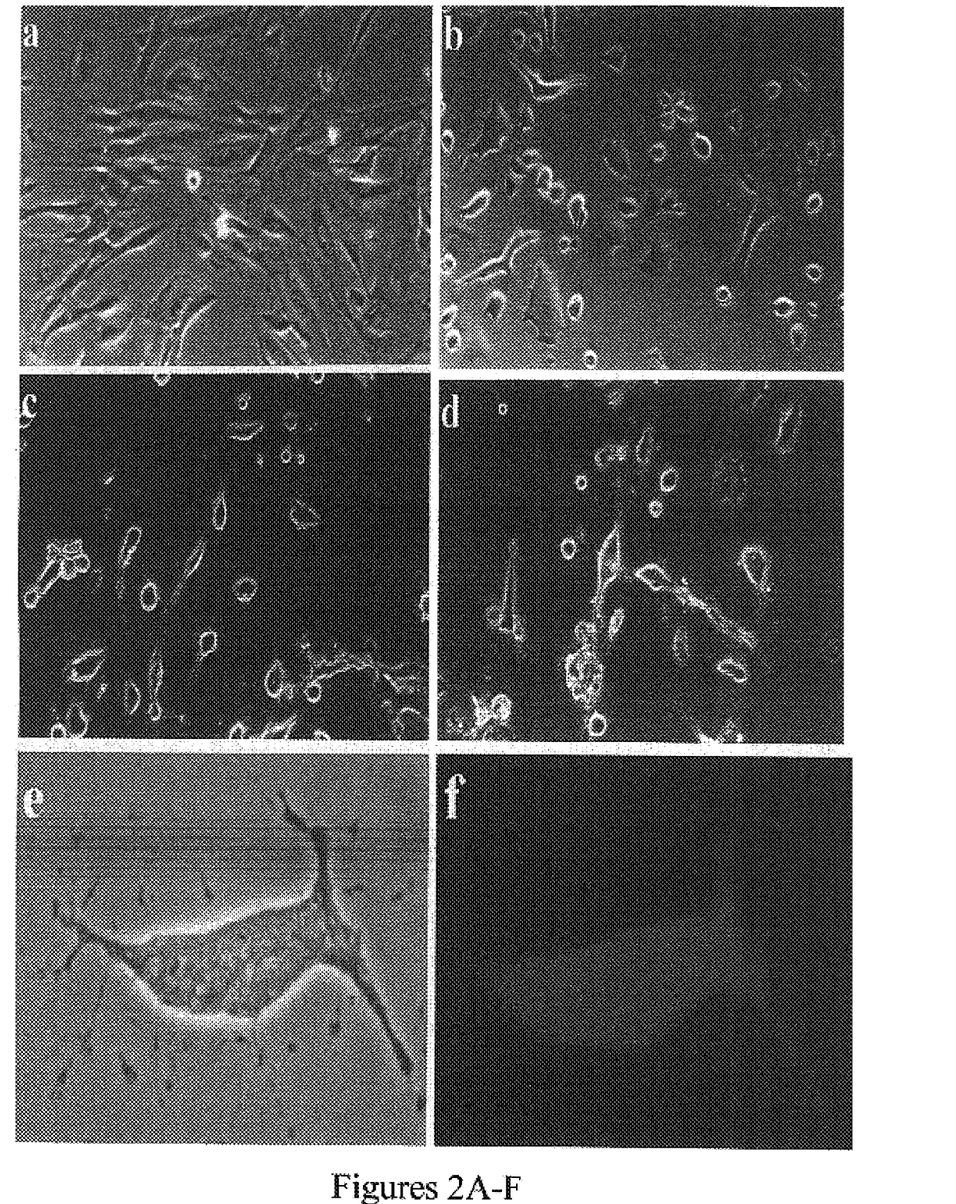
FIG. 2A is an image showing AFMSCs at fifth-passage culture before neuronal induction.

Refer to FIG. 2A, which is an image showing AFMSCs at fifth-passage culture before neuronal induction; FIG. 2B, which is an image showing the cytoplasm of the cells retract toward the nucleus and forms a rounded cell body after 6 hours of pre-treatment, and FIG. 2C, which is an image showing an apparent neuron-like cell with a long axon-like process observed after 4 hours of serum-free induction.

Initially, cytoplasm in some of the AFMSCs retracted toward the nucleus and began to form a rounded cell body within several hours of pre-treatment as shown in FIGS. 2B and 2C.

Refer to FIG. 2D, which is a diagram showing a typical neuron-like cell with multiple neuritis after 4.5 hours of serum-free induction.

As illustrated in FIG. 2D, after incubation to a serum-free condition, the morphologic changes increased progressively and then the neurite outgrowth was observed at 2–3 hours.

Refer to FIG. 2E, which is an image showing a neuron-like cell before staining, and FIG. 2F, which is an image showing positive immunofluorescence stain of TuJ1, a marker for neuronal differentiation.

At 5 hours, as illustrated in FIG. 2E, the induced cells exhibited a positive immunofluorescence stain for neuron-specific class III β-tubulin, as illustrated in FIG. 2F. Yet, non-treated control cultures did not show any of the above differentiations.

Figure 3:
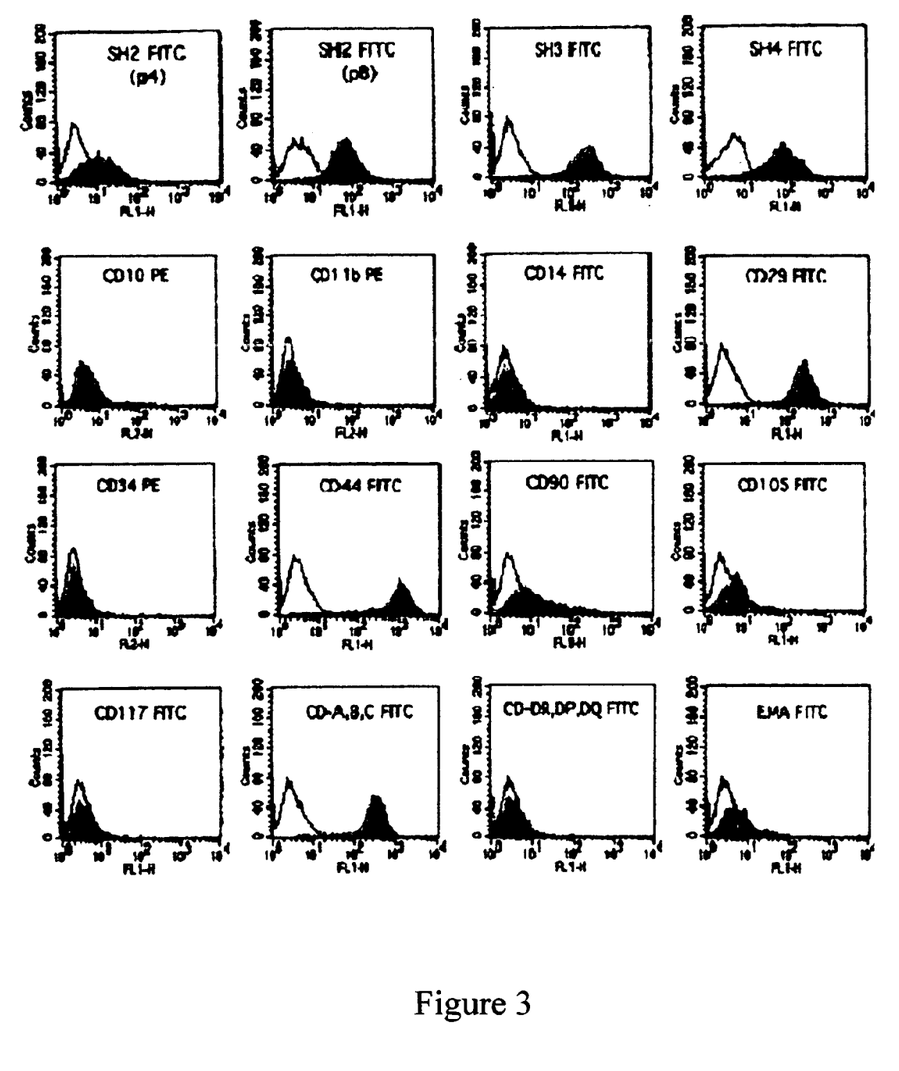
FIG. 3 is a collection of graphs showing phenotypic characteristics of AFMSCs.

Refer to FIG. 3, which is a collection of graphs showing phenotypic characteristics of AFMSCs.

FIG. 3 shows the cell surface antigenic characteristics of the cultured AFMSCs at passage 4–8 by flow cytometry. The analyses revealed that the expression of surface antigens, such as SH2 (passage 8), SH3, SH4, CD29, CD44 and HLA-A,B,C (MHC class I) was strongly positive; SH2 (passage 4), CD90 and CD105 were low positive, but CD10, CD11b, CD14, CD34, CD117, HLA-DR,DP,DQ (MHC class II) and EMA were negative. Further characterization studies were performed using RT-PCR and immunocytochemical staining for the detection of Oct-4 expression, which is a transcription factor expressed in undifferentiated embryonic stem cells.

Figure 4:
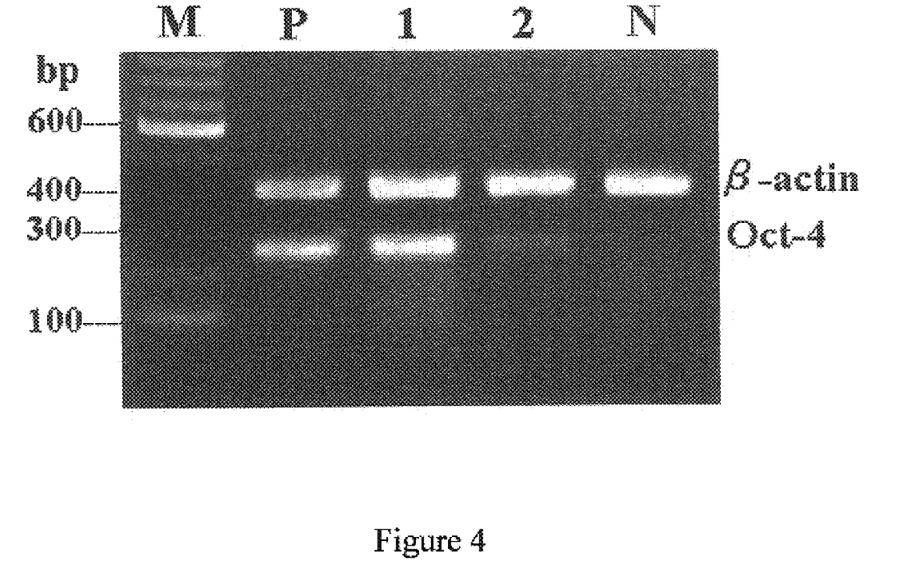
FIG. 4 is an image showing AFMSCs express Oct-4 mRNA.

Refer to FIG. 4, which is an image showing AFMSCs express Oct-4 mRNA, and FIGS. 5A–5D, which are images showing immunocytochemical analyses revealed a subpopulation of Oct-4 protein expression cells found in the culture of AFMSCs.

As illustrated in FIG. 4, RT-PCR analyses showed that OCT-4 mRNA expression was detectable in the cultured AFMSCs, and the PCR products of β-actin served as an internal control. In the figure, column P is the positive control with NTERA-2 c1.D1 cells. Column 1 and column 2 are two independent samples of cultured AFMSCs. Column N is negative control with MRC-5 cells.

In addition to Oct-4 mRNA expression detected in all 20 independent cases of AFMSCs as shown in FIG. 4, Oct-4 protein expression was also noted in a subpopulation of our cultured AFMSCs as shown in FIG. 5D.

Figure 5A:
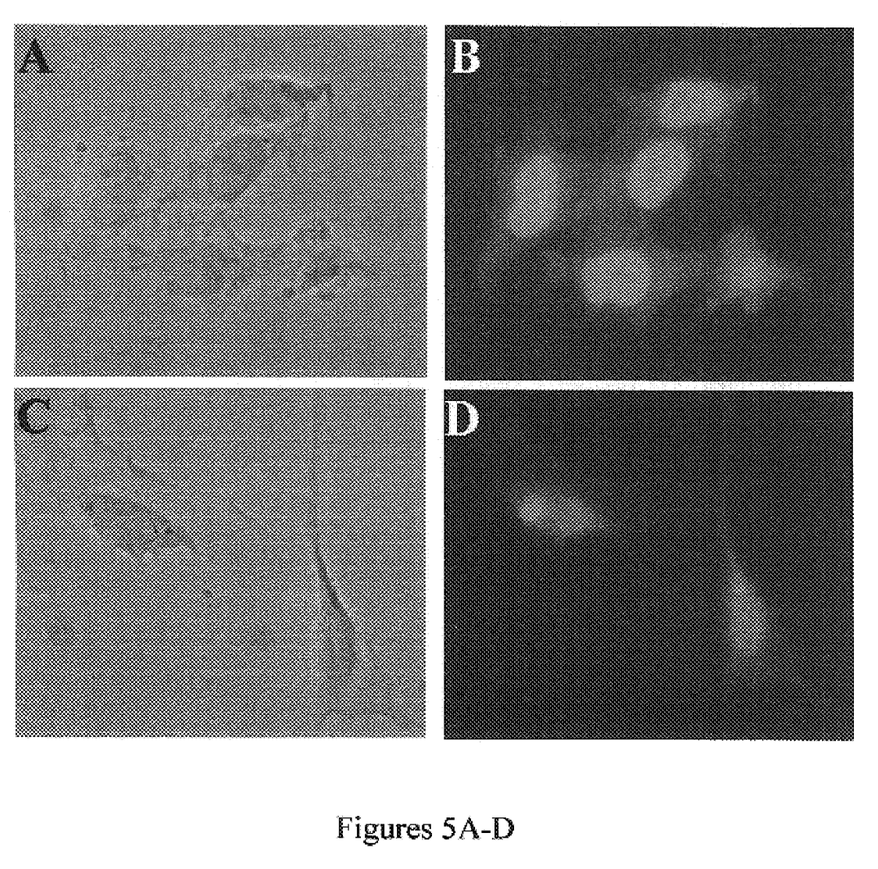
FIG. 5A is an image showing the light phase of NTERA-2 c1.D1 cells.

FIG. 5A illustrates the light phase of NTERA-2 c1.D1 cells. FIG. 5B illustrates Oct-4 immunocytochemical staining of NTERA-2 c1.D1 cells. The light phase of AFMSCs is shown in FIG. 5C and immunocytochemical staining of Oct-4 positive cells in cultured AFMSCs is shown if FIG. 5D.

As described above, the present invention demonstrates that MSCs can be successfully isolated and expanded from second-trimester amniotic fluid obtained by routine amniocentesis, and they maintain the capacity to differentiate not only into mesodermal cell types but also into ectodermal neuron cells in vitro. Considering the easy access to samples for stem cells culture, the greater potential of cellular therapy using fetal stem cells and the feasibility of intrauterine fetal tissue engineering, amniotic fluid may provide an excellent alternative source for investigation of human MSCs and their potential therapeutic applications.

It will be apparent to those skilled in the art that various modifications and variations can be made to the present invention without departing from the scope or spirit of the invention. In view of the foregoing, it is intended that the present invention cover modifications and variations of this invention provided they fall within the scope of the invention and its equivalent.

What is claimed is:

1. A method for harvesting mesenchymal stem cells from human amniotic fluid comprising:
   (a) culturing a plurality of human amniotic fluid amniocytes including the steps of:
      (i) setting up primary amniocyte cultures comprising a plurality of adherent human amniotic fluid cells and a supernatant containing a plurality of non-adherent human amniotic fluid cells and a liquid medium; and
      (ii) collecting said non-adherent human amniotic fluid cells in the supernatant; and
   (b) culturing a plurality of mesenchymal stem cells including the steps of:
      (i) centrifuging the non-adherent human amniotic fluid cells;
      (ii) plating the centrifuged non-adherent human amniotic fluid cells from step b(i) in an alpha-modified Minimum Essential Medium supplemented with fetal bovine serum in a culture flask; and
      (iii) incubating said plated non-adherent human amniotic fluid cells from step (b)(ii) with humidified $CO_2$ to promote mesenchymal stem cell growth.

2. The method for harvesting mesenchymal stem cells from human amniotic fluid as recited in claim 1 wherein said human amniotic fluid is obtained during a second trimester of pregnancy.

3. The method for harvesting mesenchymal stem cells from human amniotic fluid of claim 1 further comprising plating the non-adherent human amniotic fluid cells from step b(i) wit a predetermined concentration of basic fibroblast growth factor.

4. The method for harvesting mesenchymal stem cells from human amniotic fluid of claim 3 wherein said predetermined concentration of basic fibroblast growth factor is 1–20 ng/ml.

5. The method for harvesting mesenchymal stem cells from human amniotic fluid of claim 1 whereby the incubating is performed at 37 degrees Celsius.

6. The method for harvesting mesenchymal stem cells from human amniotic fluid of claim 1 wherein the humidified $CO_2$ comprises 5% humidified $CO_2$.

7. The method for harvesting mesenchymal stem cells from human amniotic fluid of claim 1 wherein the alpha-modified Minimum Essential Medium comprises 5–15 ml of alpha-modified Minimum Essential Medium.

8. The method for harvesting mesenchymal stem cells from human amniotic fluid of claim 1, wherein the fetal bovine serum comprises 10–20% fetal bovine serum.

9. The method for harvesting mesenchymal stem cells from human amniotic fluid as recited in claim 1, further comprising:
   performing a phenotypic characteristic analysis of the amniotic fluid-derived mesenchymal stem cells wherein said phenotypic characteristic analysis is chosen from the group consisting of flow cytometry analysis, immunocytochemical analysis, reverse transcription-polymerase chain reaction ("RT-PCR"), and combinations thereof.

10. The method of harvesting mesenchymal stem cells from human amniotic fluid as recited in claim 9 wherein the reverse transcription-polymerase chain reaction is primed with a DNA primer selected from the group consisting of

5'-CGTGAAGCTGGAGAAGGAGAAGCTG-3'    (SEQ ID NO: 1);

5'-CAAGGGCCGCAGCTTACACATGTTC-3'    (SEQ ID NO: 2);

5'-TGGCACCACACCTTCTACAATGAGC-3'    (SEQ ID NO: 3);

5'-GCACAGCTTCTCCTTAATGTCACGC-3'    (SEQ ID NO: 4);

and combinations thereof, and with said flow cytometry analysis being performed according to the steps of:
   (a) trypsinizing the amniotic fluid-derived mesenchymal stem cells;
   (b) staining said trypsinized cells from step (a) with a plurality of fluoroscein-isothio-cyanate ("FITC")- or phycoerythrin ("PE")- conjugated antibodies against CD10, CD11b, CD34, CD90, HLA-A,B,C, HLA-DR, DP, DQ; CD14, CD29, CD44, CD105, CD117; and SH2, SH3, SH4; and
   (c) analyzing said trypsinized and stained amniotic fluid-derived mesenchymal stem cells from step (a) using a flow cytometer.

11. A method for harvesting a plurality of amniotic fluid-derived mesenchymal stem cells from human amniotic fluid comprising:
   (a) culturing a plurality of amniocytes harvested from human amniotic fluid including the steps of:
      (i) setting up four primary anniocyte cultures, said primary amniocyte cultures comprising a plurality of adherent human amniotic fluid cells and a supernatant containing a plurality of non-adherent human amniotic fluid cells and a liquid medium;
      (ii) collecting a plurality of non-adherent human amniotic fluid cells in the supernatant from step (a)(i); and
   (b) culturing a plurality of mesenchymal stem cells which culturing comprises:
      (i) centrifuging the plurality of non-adherent human amniotic fluid cells;
      (ii) plating the plurality of non-adherent human amniotic fluid cells in alpha-modified Minimum Essential Medium supplemented with fetal bovine serum and basic fibroblast growth factor in a culture flask; and
      (iii) incubating at 37 degrees Celsius wit 5% humidified $CO_2$ for supporting growth of mesenchymal stem cells.

12. The method for harvesting mesenchymal stem cells from human amniotic fluid of claim 11, further comprising:
   performing a phenotypic characteristic analysis of the human amniotic fluid-derived mesenchymal stem cells wherein said phenotypic characteristic analysis is chosen from the group consisting of flow cytometry analysis, immunocytochemical analysis, reverse transcription-polymerase chain reaction ("RT-PCR"), and combinations thereof, with said RT-PCR performed using a plurality of primers consisting essentially of:

5'-CGTGAAGCTGGAGAAGGAGAAGCTG-3' (SEQ ID NO: 1);

5'-CAAGGGCCGCAGCTTACACATGTTC-3' (SEQ ID NO: 2);

5'-TGGCACCACACCTTCTACAATGAGC-3' (SEQ ID NO: 3); and

5'-GCACAGCTTCTCCTTAATGTCACGC-3' (SEQ ID NO: 4).

13. The method for isolating mesenchymal stem cells from human amniotic fluid of claim 11 wherein said human amniotic fluid is harvested during a second trimester of pregnancy.

14. A method for harvesting mesenchymal stem cells from human amniotic fluid comprising;
   (a) culturing amniocytes harvested from said human amniotic fluid including the steps of:
      (i) setting up primary amniocyte cultures in tissue culture-grade dishes using Chang medium; and (ii) collecting a plurality of non-adherent amniotic fluid cells in a supernatant medium of said primary amniocyte cultures; and (b) culturing a plurality of non-adherent amniocytes from a supernatant of said amniocyte culture to form a plurality of mesenchymal stem cells which culturing comprises:

(i) centrifuging a plurality of non-adhering cells harvested from a supernatant of a culture of amniocytes from human amniotic fluid;

(ii) plating a plurality of non-adherent human amniotic fluid cells in alpha-modified Minimum Essential Medium supplemented with a fetal bovine serum and a basic fibroblast growth factor in a culture flask; and (iii) incubating said non-adherent human amniotic fluid cells from step (b) at an incubating temperature with humidified $CO_2$ to promote mesenchymal stem cell growth.

15. The method for harvesting mesenchymal stem cells from human amniotic fluid of claim 14 wherein said basic fibroblast growth factor comprises 1–20 ng/ml basic fibroblast growth factor.

16. The method for harvesting mesenchymal stem cells from human amniotic fluid of claim 14 whereby the incubating temperature is 37 degrees Celsius.

17. The method for harvesting mesenchymal stem cells from human amniotic fluid of claim 14 whereby the humidified $CO_2$ comprises 5% humidified $CO_2$.

18. The method for harvesting mesenchymal stem cells from human amniotic fluid of claim 14 whereby the alpha-modified Minimum Essential Medium comprises 5–15 ml of alpha-modified Minimum Essential Medium.

19. The method for harvesting mesenchymal stem cells from human amniotic fluid of claim 14 whereby the fetal bovine serum comprises 10–20% fetal bovine serum.

20. The method for harvesting mesenchymal stem cells from human amniotic fluid of claim 14 further comprising performing a phenotypic characteristic analysis of the amniotic fluid-derived mesenchymal stem cells.

21. The method for harvesting mesenchymal stem cells from human amniotic fluid of claim 20 wherein the phenotypic characteristic analysis is chosen from the group consisting of flow cytometry analysis, immunocytochemical analysis, reverse transcription-polymerase chain reaction, or a combination thereof.

* * * * *

SEQUENCE LISTING

```
<160> NUMBER OF SEQ ID NOS: 4

<210> SEQ ID NO 1
<211> LENGTH: 25
<212> TYPE: DNA
<213> ORGANISM: Homo sapiens

<400> SEQUENCE: 1
cgtgaagctg gagaaggaga agctg                                   25

<210> SEQ ID NO 2
<211> LENGTH: 25
<212> TYPE: DNA
<213> ORGANISM: Homo sapiens

<400> SEQUENCE: 2
caagggccgc agcttacaca tgttc                                   25

<210> SEQ ID NO 3
<211> LENGTH: 25
<212> TYPE: DNA
<213> ORGANISM: Homo sapiens

<400> SEQUENCE: 3
tggcaccaca ccttctacaa tgagc                                   25

<210> SEQ ID NO 4
<211> LENGTH: 25
<212> TYPE: DNA
<213> ORGANISM: Homo sapiens

<400> SEQUENCE: 4
gcacagcttc tccttaatgt cacgc                                   25
```